United States Patent
Miki et al.

(10) Patent No.: US 6,458,407 B1
(45) Date of Patent: Oct. 1, 2002

(54) PROCESS FOR PRODUCING ESSENTIAL OIL BY SUBCRITICAL OR SUPERCRITICAL WATER TREATMENT

(75) Inventors: Wataru Miki, Hyogo; Koichi Nakahara, Osaka; Takahisa Fujii, Kyoto; Kenzoh Nagami, Osaka; Kunio Arai, Miyagi, all of (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/445,187

(22) PCT Filed: Apr. 9, 1999

(86) PCT No.: PCT/JP99/01897

§ 371 (c)(1),
(2), (4) Date: Jan. 10, 2000

(87) PCT Pub. No.: WO99/53002

PCT Pub. Date: Oct. 21, 1999

(30) Foreign Application Priority Data

Apr. 9, 1998 (JP) ............................................ 10-097821

(51) Int. Cl.⁷ ............................. A23L 1/222; A23L 1/28

(52) U.S. Cl. ....................... 426/651; 426/429; 426/431; 426/435; 426/436; 426/489; 426/655

(58) Field of Search .................................. 426/651, 655, 426/650, 386, 387, 425, 434, 489, 431, 435, 436, 429

(56) References Cited

U.S. PATENT DOCUMENTS

| 4,497,838 A | * | 2/1985 | Bonnell ....................... 426/429 |
| 5,252,729 A | * | 10/1993 | De Crosta et al. ............ 540/18 |
| 6,001,256 A | * | 12/1999 | Hawthorne et al. ......... 210/643 |

* cited by examiner

Primary Examiner—Arthur L. Corbin
(74) Attorney, Agent, or Firm—Paul E. White, Jr.; Manelli Denison & Selter PLLC

(57) ABSTRACT

The present invention provides a novel process for producing an essential oil from a plant material. Concretely, the process produces an essential oil in a short time and by a simple procedure by treating a plant material with supercritical water or subcritical water to liberate essential oil components, which are contained in the plant material, as an ester-free essential oil, and separating and purifying this essential oil.

11 Claims, No Drawings

PROCESS FOR PRODUCING ESSENTIAL OIL BY SUBCRITICAL OR SUPERCRITICAL WATER TREATMENT

This application is the national phase of international application PCT/JP99/01897 filed Apr. 9, 1999 which designated the U.S.

TECHNICAL FIELD OF THE INVENTION

The present invention relates to a process for producing an essential oil from a plant material. More particularly, the invention relates to a process for producing an essential oil, which is free of esters and consists essentially of terpene, in a short period of time and by a simple procedure involving extraction of an essential oil with water in a supercritical state or subcritical state.

PRIOR ART

Essential oils are volatile oils obtained from flowers, buds, leaves, branches, trunks, roots, etc. of various plants and having characteristic aromas. These oils are normally composed of several types of terpenes and aromatic compounds, and have osmophores such as alcohol, phenol and ester. Essential oils are utilized as raw materials for perfumes, and have been obtained by methods such as steam distillation, extraction, and expression.

Steam distillation is a method of distillation which, in the presence of steam, distills off liquids with high boiling points at considerably lower temperatures than the boiling points. Extraction is a method for dissolving certain components into a solvent, and separating and recovering the components. Expression combines squeezing with steam distillation or extraction with an organic solvent to obtain components in distilled form while squeezing the material.

In essential oils collected by these conventional methods, components containing esters are present. The esters are mainly acetic acid esters, which pose the problem of undergoing changes in properties owing to de-esterification which takes place during storage of the essential oils. There is also the drawback that the essential oils tend to undergo oxidative deterioration and acidic decomposition due to acetic acid per se which results from the de-esterification reaction. Furthermore, those conventional methods all give low yields, thus necessitating the use of multiple steps for treatment. Consequently, they are defective in that collection of essential oils by distillation cannot be completed in short periods of time. All of the conventional methods, moreover, possesses the shortcoming from an environmental viewpoint, that squeeze leavings of plant materials emerge as waste.

Various application studies are under way with regard to extraction, purification, synthesis and decomposition using supercritical fluids. For supercritical water, studies on its capacity to detoxify PCB and dioxin (Japanese Patent Public Disclosure (Kokai) No. 327678/97) are being carried out, and its degradation reaction of biomass is also being investigated. Japanese Patent Public Disclosure (Kokai) No. 31000/93 reports a method which selectively hydrolyzes or pyrolyzes natural or synthetic high molecular compounds with the use of supercritical water as a solvent to decompose the polymers into their constituent units or into approximately oligomeric combinations of the constituent units. Examples of this method include the formation of glucose from cellulose contained in large amounts in polymeric resources, such as paper, wood and straw, and conversion of lignin-derived specimens into low molecular compounds. Japanese Patent Public Disclosure (Kokai) No. 268166/97 describes a method for producing various amino acids by hydrolyzing proteins with water present in a supercritical state.

However, it has not been known that it is possible to obtain essential oils by treating plant materials with water present in a supercritical state.

SUMMARY OF THE INVENTION

It is an object of the present invention to provide a novel process for producing an essential oil from a plant material.

It is another object of the present invention to provide a process for producing an essential oil from a plant material, the essential oil being free of esters and consisting essentially of terpenes, and an essential oil produced by the process. According to the process of this invention, an essential oil having a composition unobtainable by conventional methods, such as steam distillation, can be provided.

It is a further object of the invention to provide a process for producing an essential oil, in which process an extraction procedure is completed in a very short time (within several minutes), as compared with conventional methods, such as steam distillation, generally used to obtain essential oils.

It is a still further object of the invention to provide a process for producing an essential oil, which process does not discharge waste generated as squeeze leavings as results from conventional methods such as steam distillation.

DETAILED DESCRIPTION OF THE INVENTION

The present invention is a process for producing an essential oil in a short period of time and by a simple procedure, the process comprising treating a plant material with supercritical water or subcritical water to liberate essential oil components, which are contained in the plant material, as an ester-free essential oil; and separating and purifying the essential oil.

Plant Materials Used

Examples of plants used to produce an essential oil in accordance with the present invention include, but are not restricted to, bamboo, Japanese cedar, hinoki, Quercus crispula, cherry tree, Japanese horse chestnut, pine tree, hiba arborvitae, Japanese chestnut tree, bamboo grass, oak, paulownia, Japanese apricot, peach, maple tree, zelkova tree, wisteria, fir, elm, ginkgo, camellia, willow, mulberry, magnolia, persimmon, apricot, Chinese quince, sweet brier, rose, loquat, Japanese quince, fragrant olive, camphor tree, Japanese yew, acacia, prickly shrub of Araliaceae, amyris, Boi de Rose, and loo. Depending on the plant selected, an essential oil having various scents is obtained. Two or more of these enumerated plants may be mixed and used in the invention.

Any parts of these plants can be used, such as trunk, bark, stalk, branch, root, leaf, flower, bud, and seed. Typically, a woody portion or a floral portion is used. For example, it is preferred to use wooded-type containers which were used for the production and/or storage of fermented products and foods and drinks, as plant materials, in order to effect utilization of waste materials.

A plant material from these plants may be treated, in any size, with supercritical water. Preferably, the plant material is chopped finely to a size of about 1 cm square, or if it is a floral portion, is cut thinly, for pretreatment, and then is subjected to supercritical water treatment. More preferably, the plant material is powdered, and then subjected to supercritical water treatment.

Conditions for Supercritical Water Treatment

The process of the present invention is characterized by treating a plant material with supercritical water.

It is well known that substances can exist in three states:, as a solid, liquid or gas. If temperature and pressure are gradually increased, starting in a state in which a gas and a liquid mingle. When a certain pressure and a certain temperature (i.e., critical point) are exceeded, there exists a range in which the boundary surface between the gas and the liquid disappears, and the gas and liquid integrate as an inseparable entity, to form a fluid state. Such a fluid is called a supercritical fluid, which is a high-density fluid having properties intermediate between gas and liquid. That is, this fluid, like a liquid, dissolves various substances, and has high fluidity like a gas.

The critical point for water is a temperature of 374° C. and a pressure of 221 atmospheres. Supercritical water refers to water in a state at a temperature and a pressure in specific ranges exceeding this critical point. Supercritical water continuously varies in the values of parameters, such as density, viscosity, dielectric constant, ion product, and diffusion coefficient, depending on temperature and pressure. Solubility, an important parameter for a reaction solvent, is known to increase as density increases. Another factor related to solubility is dielectric constant, which increases with increasing density, and decreases as temperature rises. At a sufficiently high temperature, a dielectric constant becomes so small that water is almost unable to shield the electrostatic force working among ions. Under these conditions, most of the dissolved ion species are present as ion pairs. Thus, supercritical water behaves as a nonpolar substance, rather than as a polar substance. Incidentally, the pH of water in a supercritical state is 4, producing a hydrogen ion concentration of $1/10,000$, while the hydroxide ion concentration is also $1/10,000$. Hence, it will be readily apparent that the properties of this water are entirely different from those of water as a liquid.

The present invention produces an essential oil by utilizing the foregoing features of supercritical water. The invention is characterized by the ability to produce an essential oil easily and-in a short time, in comparison with conventional technologies such as steam distillation. In light of this feature of the present invention, it can be easily predicted that treatment of a plant material with subcritical water next to supercritical water would similarly be able to obtain an essential oil. Hence, references, to be made hereinbelow, to supercritical water also include subcritical water, as will be clear from the context.

During supercritical water treatment, the plant material and water are mixed, for example, at a plant material-to-water ratio of 1:about 1 to 1,000, preferably, 1:about 5 to 200. The reactor may be any container suitable for supercritical water treatment, and may be selected, as desired, according to the scale of production. For example, a closed container (preferably one made of a metal such as SUS alloy) with a capacity of about 1 ml to 10 liters, preferably about 10 ml to 1 liter, is used. This container is charged with about 30 to 40% (V/V), preferably 32 to 35% (V/V), of water, and the plant material is added at the above-mentioned ratio. To produce an essential oil, treatment is preferably performed in an anaerobic state. For this purpose, it is advisable to deaerate the inside of the container, or fully purge the inside of the container and water with an inert gas such as nitrogen or argon, followed by closing the container. Treatment is performed under conditions under which water is in a supercritical state at a temperature of about 374° C. (pressure at this time is about 221 atmospheres or more) to about 500° C. (about 300 atmospheres or more), or under conditions under which water is in a subcritical state at a temperature exceeding about 300° C. (exceeding about 150 to 200 atmospheres). The treatment time is within about 30 minutes, preferably within about 2 minutes.

Separation and Purification of Essential Oil

The plant material treated with water in a supercritical state is cooled by a means such as rapid cooling of the reactor containing the material with iced water or the like. After making sure that the temperature has been sufficiently lowered, the reactor is opened. Normally, water soluble substances are recovered as an aqueous solution, while liposoluble substances adhere to the wall surface in a tarry form. Thus, the water surface is washed with water first, and then is sprinkled with a water-absorbing salt, such as anhydrous sodium sulfate or calcium chloride, for dehydration. Then, an essential oil is recovered with the use of a hexane-diethyl ether mixture (the mixing ratio is basically 1:1, but can be selected suitably depending on the plant material) as a solvent. Other examples of usable solvents are a petroleum ether-diethyl ether mixture, and a petroleum benzine-diethyl ether mixture. The recovered essential oil is purified, as required, with activated charcoal or an adsorbent carrier, and used according to the purpose of use. Purification methods rely on, but are not restricted to, various chromatographic techniques, use of various separation membranes, and use of various resins.

The thus obtained essential oil can be used, unchanged, as a perfume, or as a raw material for foods or cosmetics. Its application to pharmaceuticals can also be expected.

The tarry substance after extraction of the essential oil is likely to contain other useful components. For example, aromatic compounds, including phenylpropanoids, pyrogallol derivatives, and pyrocatechol derivatives, can be recovered by further extraction with organic solvents, such as alcohol, acetone and acetonitrile.

The aqueous solution recovered from inside the reactor may contain low molecular compounds such as glucose or lignin. These compounds may be isolated separately, if desired.

The present invention will now be described more concretely by way of the following Examples, which in no way limit the invention.

EXAMPLE 1

A magnolia material was cut thinly with a saw, and powdered. A reactor (internal capacity 10 ml) of SUS alloy was charged with 3.25 ml of distilled water, and 500 mg of the magnolia material powder was added. Then, the inside of the reactor was purged fully with nitrogen, and the reactor was rapidly closed. The reactor was placed in a separately prepared resin bath (maintained in a mantle heater) kept at 380° C., and reaction was performed for 45 seconds at 221 atmospheres or more. Then, the reactor was dipped in iced water for cooling. When the temperature of the contents reached 40° C., the reactor was opened. An aqueous solution was removed, whereafter the wall was sprinkled with 3 g of anhydrous sodium sulfate, and allowed to stand for 5 minutes. Then, essential oil components were immediately extracted with about 10 ml of a hexane-diethyl ether (1:1) mixture. The essential oil components were treated with activated charcoal having a final concentration of 2,000 ppm. Their composition was examined by high performance liquid chromatography (carrier; Nakarai Tesk silica gel normal phase, mobile phase; 50-minute gradient elution with hexane to diethyl ether, flow rate 1 ml/min, detection wavelength 280 nm), and gas chromatography (carrier; Cellite:Carbowax 1500=10:2, temperature; 170° C., carrier gas; nitrogen gas, flow rate 0.6 kg/cm$^2$).

The results are shown in Table 1. As the results indicate, ester compounds and bornyl acetate which are obtained as main components by steam distillation were not detected, but borneol was obtained as a main component instead. The oil yield based on the magnolia material was about 5 times that obtained with steam distillation (steam distillation; 0.6%, process of the invention; 3.1%).

TABLE 1

Essential components of magnolia material (compared with the results with steam distillation as control)

| | Process of the invention | (%) Steam distillation |
|---|---|---|
| Pinenes | 1.4 | 1.2 |
| Camphene | 2.0 | 2.0 |
| Myrcene | 0.8 | 0.7 |
| Limonene | 0.6 | 0.5 |
| p-Cymene | 1.2 | 1.2 |
| Borneol | 9.0 | 3.5 |
| Camphor | 1.1 | 1.1 |
| Bornyl acetate | — | 5.0 |
| Methyl ketones | 15.5 | 15.2 |
| Cadinols | 3.0 | 3.2 |
| Others | 65.4 | 66.4 |

EXAMPLE 2

A hinoki material was cut thinly with a saw, and powdered. A reactor (internal capacity 10 ml) of SUS alloy was charged with 3.25 ml of distilled water, and 500 mg of the hinoki material powder was added. Then, the inside of the reactor was purged fully with nitrogen, and the reactor was rapidly closed. The reactor was placed in a separately prepared resin bath (maintained in a mantle heater) kept at 380° C., and reaction was performed for 45 seconds at 221 atmospheres or more. Then, the reactor was dipped in iced water for cooling. When the temperature reached 40° C., the reactor was opened. An aqueous solution was removed, whereafter the wall was sprinkled with 3 g of anhydrous sodium sulfate, and allowed to stand for 5 minutes. Then, essential oil components were immediately extracted with a hexane-diethyl ether (1:1) mixture. The extract was treated with activated charcoal having a final concentration of 2,000 ppm, and then the solvents were distilled off by means of an evaporator to obtain an essential oil. The resulting essential oil had a characteristic odor.

EXAMPLE 3

Petals of a rose were sliced to a size of 2 to 3 mm with scissors. A reactor (internal capacity 10 ml) of SUS alloy was charged with 3.25 ml of distilled water, and 500 mg of the petal slices were added. Then, the inside of the reactor was purged fully with nitrogen, and the reactor was rapidly closed. The reactor was placed in a separately prepared resin bath (maintained in a mantle heater) kept at 380° C., and reaction was performed for 45 seconds at 221 atmospheres or more. Then, the reactor was dipped in iced water for cooling. When the temperature reached 40° C., the reactor was opened. An aqueous solution was removed, whereafter the wall was sprinkled with 3 g of anhydrous sodium sulfate, and allowed to stand for 5 minutes. Then, essential oil components were immediately extracted with a hexane-diethyl ether (1:1) mixture. The extract was treated with activated charcoal having a final concentration of 2,000 ppm, and then the solvents were distilled off by means of an evaporator to obtain an essential oil. The resulting essential oil had a characteristic odor.

EFFECTS OF THE INVENTION

The process of the present invention can obtain an essential oil efficiently and very easily in a short period of time, as compared with steam distillation.

Furthermore, the process of the invention cuts ester linkages, thus making it possible to extract an essential oil free of esters and consisting essentially of terpenes. Esters in essential oils are mainly acetic acid esters. However, the essential oil extracted by the process of the present invention is characterized by difficulty in undergoing oxidative deterioration and acidic decomposition due to acetic acid per se which has resulted from de-esterification reaction occurring during its storage. Considerable amounts of acetic acid esters are present in plant materials. Treatment with water in a supercritical state makes acetic acid water-soluble, and bornyl acetate, for example, is recovered into the essential oil as unsaponifiable borneol. The essential oil produced by the process of the present invention, which has such features, is free of esters, and thus is resistant to oxidation. Moreover, the essential oil is kept from acidic deterioration by acetic acid released during storage. Thus, compared with essential oils obtained by conventional methods, the essential oil of the present invention is highly preservable. Furthermore, this essential oil is free from an ester-like odor, so that its odor as a whole is characteristically different from the odors of essential oils obtained by steam distillation. Besides, the essential oil of the invention is stable in polarity, and excellent in the ease of handling. Thus, it is suitable for use as a raw material for cosmetics and foods.

When an essential oil is produced by the process of the present invention, waste as squeeze leavings discharged by conventional methods does not appear. Thus, the invention provides an environmentally-friendly technology.

What is claimed is:

1. A process for producing a plant-derived essential oil which is free of esters, comprising treating a plant material with supercritical water under conditions sufficient to form an extract and isolating an essential oil free of esters from said extract.

2. The process of claim 1, wherein the essential oil consists essentially of terpene.

3. The process of claim 2 for producing a plant-derived essential oil, comprising heating a plant material, together with water, in a pressurized container at a pressure of 150 to 300 atmospheres and a temperature of 300 to 500° C.; then cooling the inside of the container to about 100° C. or lower; extracting a tarry substance, which has been formed, with an organic solvent selected from the group consisting of a hexane-diethyl ether mixture, a petroleum ether-diethyl ether mixture and a petroleum benzine-diethyl ether mixture; and isolating an essential oil from the extract.

4. The process of claim 3, wherein the heating at a pressure of 150 to 300 atmospheres and a temperature of 300 to 500° C. is performed for 30 minutes or less after the container is deaerated or purged with an inert gas.

5. The process of claim 4, wherein the plant material is a woody portion or a floral portion which has been chopped finely, cut thinly, or powdered.

6. The process of claim 5, wherein 1 part by volume of the plant material is heated together with 1 to 1,000 parts by volume of water in the pressurized container.

7. The process of claim 5, wherein 1 part by volume of the plant material is heated together with 2 to 200 parts by volume of water in the pressurized container.

8. The process of claim 3, wherein the heating at a pressure of 150 to 300 atmospheres and a temperature of 300 to 500° C. is performed for 2 minutes or less after the container is deaerated or purged with an inert gas.

9. The process of claim 8, wherein the plant material is a woody portion or a floral portion which has been chopped finely, cut thinly, or powdered.

10. The process of claim 9, wherein 1 part by volume of the plant material is heated together with 1 to 1,000 parts by volume of water in the pressurized container.

11. The process of claim 9, wherein 1 part by volume of the plant material is heated together with 2 to 200 parts by volume of water in the pressurized container.

* * * * *